United States Patent [19]

Visconti

[11] 4,112,939
[45] Sep. 12, 1978

[54] EVAPORATING MIXER FOR VOLATILE ANAESTHETICS

[75] Inventor: Matteo Visconti, Milan, Italy
[73] Assignee: Soxil S.p.A., Milan, Italy
[21] Appl. No.: 753,352
[22] Filed: Dec. 21, 1976
[51] Int. Cl.² .................................. A61M 17/00
[52] U.S. Cl. ..................................... 128/186
[58] Field of Search ............ 128/188, 186, 187, 173.3, 128/192, 194, 195, 205, 209, 210, 197; 261/78 R, 78 A, DIG. 27, DIG. 65, 108, 113; 222/193

[56] References Cited

U.S. PATENT DOCUMENTS 3,851,645 12/1974 Connel ............................. 128/188

FOREIGN PATENT DOCUMENTS 557,103 2/1957 Italy ........................................... 128/188
519,203 3/1940 United Kingdom ...................... 128/188
26,691 of 1914 United Kingdom ...................... 128/209
977,894 12/1964 United Kingdom ...................... 128/186

Primary Examiner—Robert W. Michell
Assistant Examiner—Henry J. Recla
Attorney, Agent, or Firm—Cushman, Darby & Cushman

[57] ABSTRACT

A mixing evaporator is disclosed, of the kind in which a breathable gas mixture is admixed, in the desired proportions, with vapors of an anaesthetic liquid, said gas mixture being compelled to sweep over the liquid level of the anaesthetic to strip vapors therefrom, the improvement consisting in that the gaseous mixture sweeping the anaesthetic liquid is compelled to travel along a sinuous path thereon. The result is obtained by a system of radial paddles having staggered openings so that the gaseous mixture becomes more and more enriched with anaesthetic liquid vapors as it proceeds towards the outlet port.

2 Claims, 7 Drawing Figures

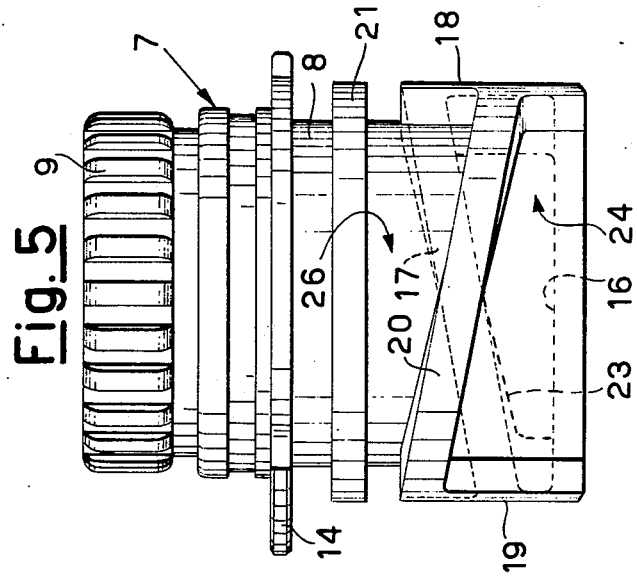
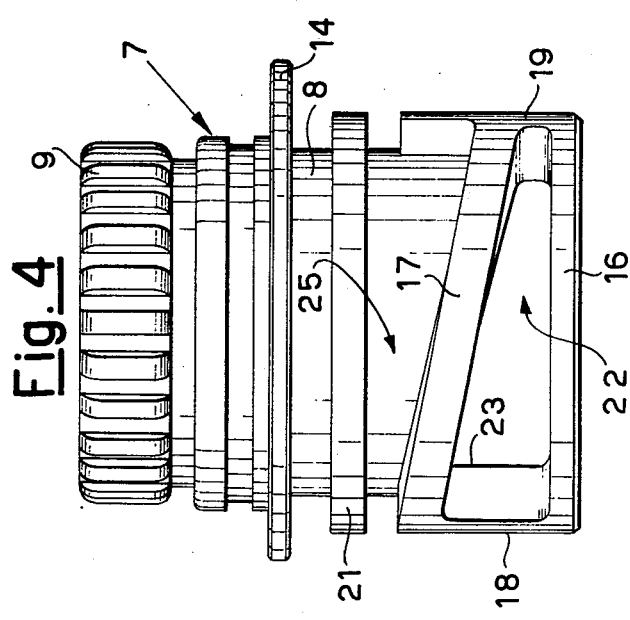
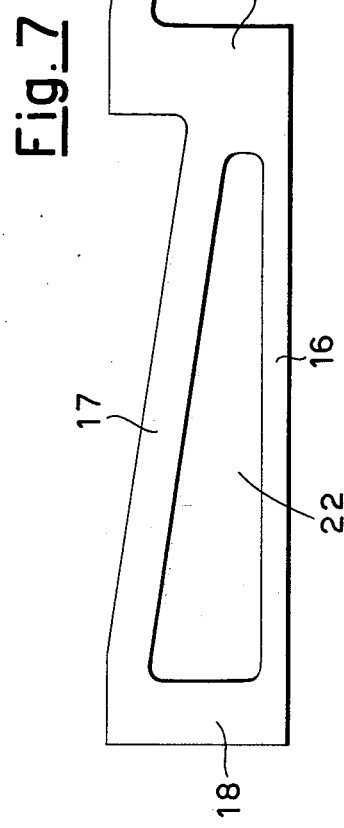

EVAPORATING MIXER FOR VOLATILE ANAESTHETICS

This invention relates to a mixing evaporator for volatile anaesthetics, that is, a device which causes the evaporation of a liquid vaporizable anaesthetic product (such as fluotane or enfluorance) in variable proportions with a flux of a breathable gaseous product (for example one containing air, oxygen and nitrogen suboxide) which sweeps said liquid.

The conventional devices of this kind comprise a vessel for containing the anaesthetic product, said device having an upper inlet port for the flux of breathable product and an upper outlet port for the same flux of breathable product, supplemented by an anaesthetic product is adjustable proportions. The determination of the proportional ratio of said products is entrusted to a rotatable body which is housed in the vessel aforementioned, which is so shaped as to define between the inlet and the outlet ports aforesaid two communication paddageways which can be complementarily throttled by a rotation of such rotatable body about the vertical axis thereof. While either passage defines, between the inlet and outlet ports, a direct communation which enables a portion of the incoming breathable product directly to reach the outlet without being supplemented with the anaesthetic product, the other passageway defines between the same ports an additional communication which is obtained through a deflected route, the latter route comprising a path portion at the same level, or so, of the anaestheic product, in which the residual fraction of the breathable product is compelled to sweep the underlying anaesthetic product so as to cause the evaporation thereof and to strip therefrom the vapors so produced.

The principle object of the present invention is the one of providing an evaporating mixer of the kind referred to above, in which the path portion at the level of the anaesthetic product is so shaped as to ensure an increased contact surface between the breathable product and the anaesthetic product.

According to the invention, such an object is achieved by the instrumentality of a mixing evaporator which is characterized in that the above mentioned portion of path at the same level as the anaesthetic product is so provided as to define a labyrinth-like route.

More detailedly, such a labyrinth-like route is preferably defined in the interior of a cylindrical body which is partially immersed in the anaesthetic product, said cylindrical body comprising two coaxial cylindrical walls having a vertical axis, there being defined between said walls an annular space which is closed at the top and is open at the bottom, said annular space being in communication with an upstream portion and a downstream portion of said deflected path in correspondence of two ends of said space which are defined at the two sides of a radial partition wall, said space being made winding by a succession of paddles which exhibit alternately arranged openings in correspondence with their inner and outer ends.

In order to afford a greater clarity, a preferred embodiment of the mixing evaporator according to the invention is shown by way of example, in the accompanying drawings, the description of such embodiment being given in more detail hereinafter.

In the drawings:

FIG. 4 is an elevational view of the cylindrical head of the rotatable body intended variably to determine the proportionality of admixture between the breathable and the anaesthetic product.

FIG. 5 shows the same cylindrical head as viewed from the opposite side.

FIG. 7 shows the development on a planar surface of the flange groups of the cylindrical head, which permits to throttle the deflected flux of the breathable product as a function of the orientation of the rotatable body in angular direction, the cylindrical head being an integral part of the rotatable body.

Figure 1:
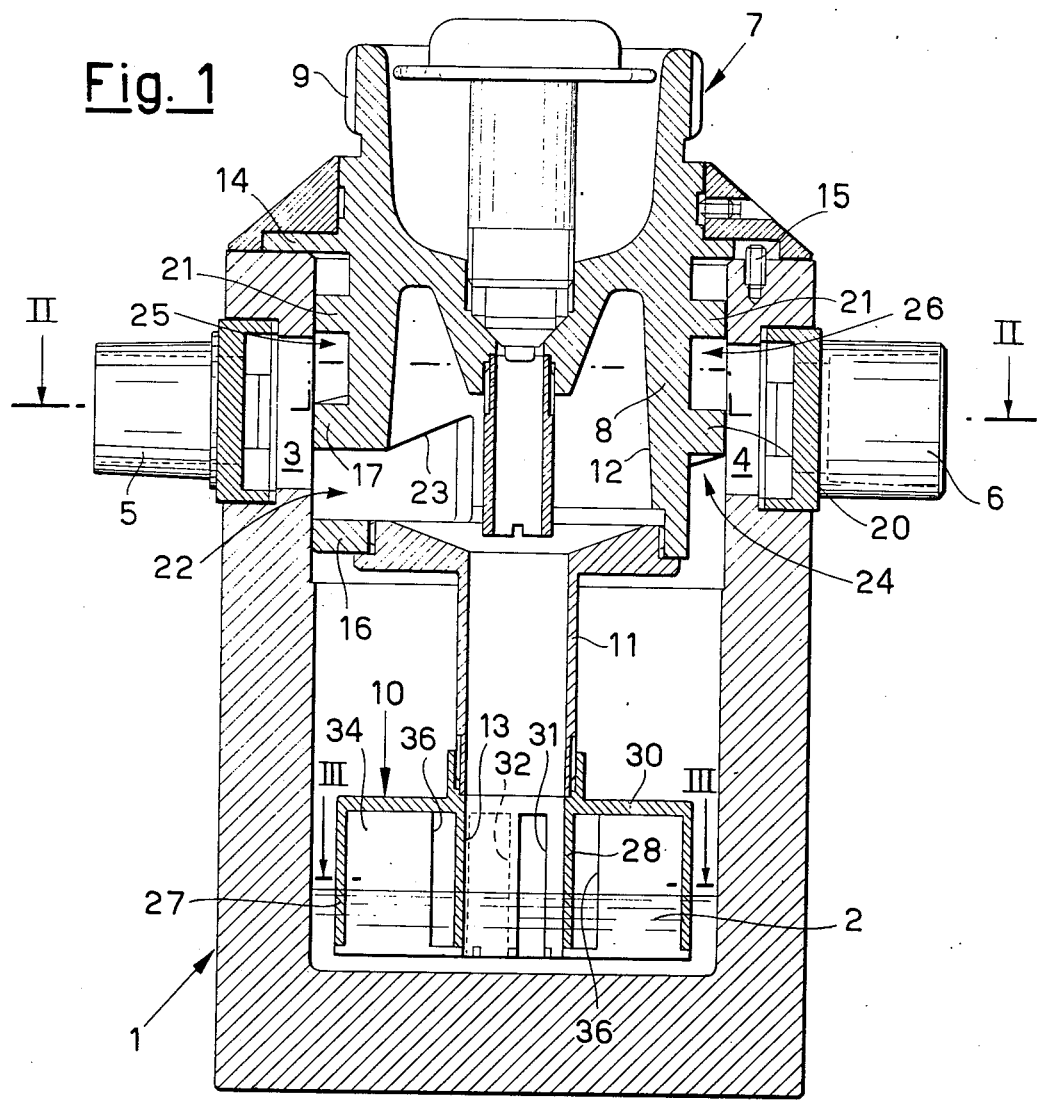
FIG. 1 shows a cross-sectional elevation view, taken along the line 1—1 of FIG. 2, of the preferred embodiment of the mixing evaporator according to the present invention.
Figure 2:
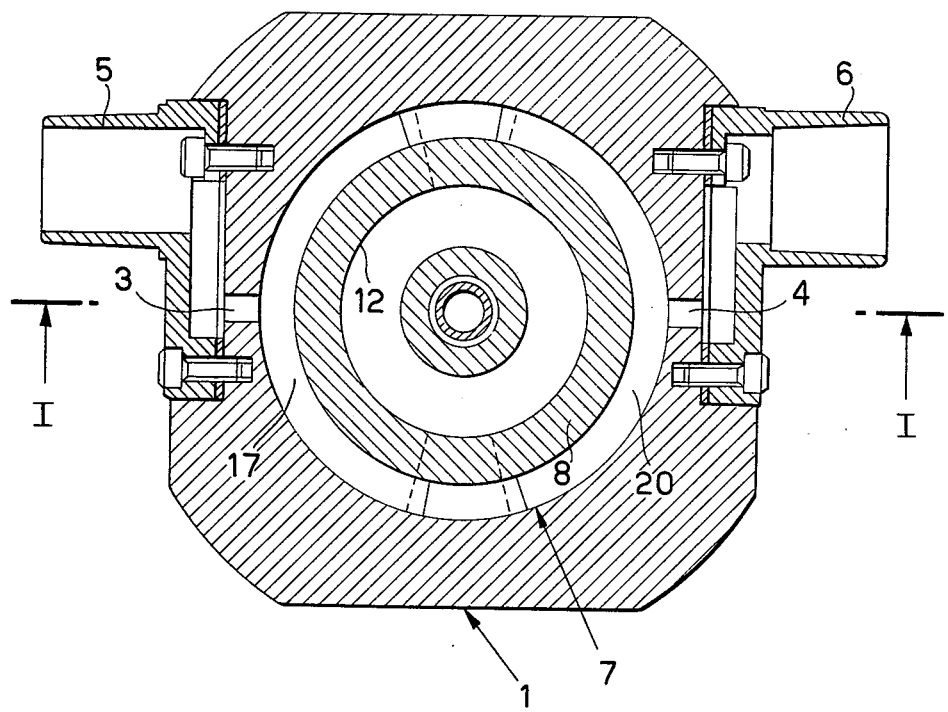
FIG. 2 shows the same mixing evaporator in horizontal cross-sectional view taken along the line II—II of FIG. 1.

The mixing evaporator shown in the drawings, and more particularly in its assembly in FIGS. 1 and 2, comprises a cylindrical vessel 1, on the bottom of which a certain quantity is collected of a liquid and vaporizable anaestetic product 2, for example fluotane or enfluorane.

In the front portion of the vessel 1, in diametrically opposite positions, there are formed two slots 3 and 4, equipped with a mouth each, 5 and 6, respectively, through the first of which a stream of breathable gaseous product can enter (such as a mixture containing oxygen and nitrogen protoxide) to be supplemented with an anaesthic product, and though the second of which the same stream of breathable product can emerge, but supplemented with an anaesthetic product.

In the interior of the vessel 1 a rotatable body 7 is housed, which is coupled to the vessel in such a way as to be rotatable about the vertical symmetry axis of the vessel and of the rotatable body as well. The rotatable body is substantially composed by three portions which are made integral with each other, and precisely by a flanged cylindrical head 8 arranged at the height of the inlet slots or ports 3 and 4 and equipped with a manipulation hand-wheel 9, by a cylindrical body 10, which is partially dipping in the anaesthetic product 2 and by an axial connection tube 11 which is intended to afford a constant communication between and intermediate chamber 12 of the cylindrical head 8 and a cylindrical chamber 13 in the interior of the cylindrical body 10.

Figure 6:
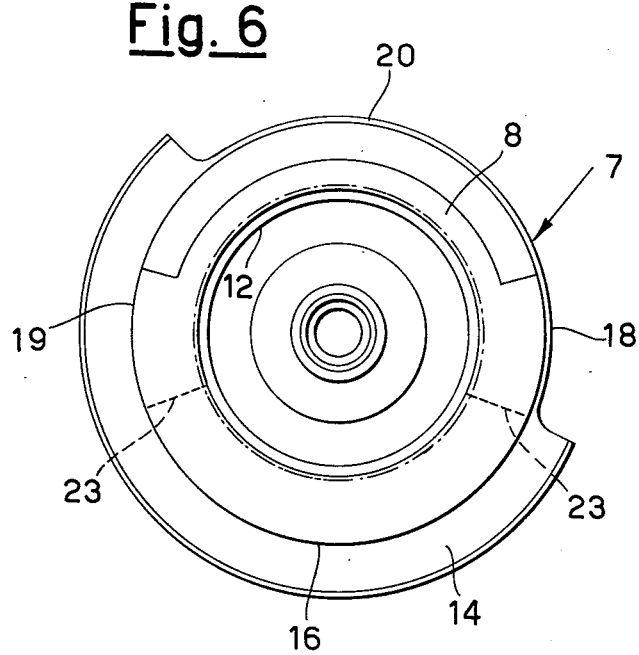
FIG. 6 shows the cylindrical head as viewed in plan from below.

As can be seen in FIGS. 4 and 5, the cylindrical head 8 is equipped with a certain number of outer flanges which are arranged at different levels with respect to the axial outline of the cylindrical head in question. Of these flanges, one, indicated with the reference numeral 14, has a width of about 205 angular degrees (FIG. 6) and is intended only to define the ends of the angular stroke of the rotatable body 7 in combination with a fixed abutment 15 (FIG. 1), whereas all the other flanges, indicated by the reference numerals 16, 17, 18, 19, 20 and 21, to be described in detail hereinafter, serve to define, in combination with the other component parts of the rotatable body 7, two communication passageways, which can complementarily be throttled, between the inlet and outlet slots or ports, 3 and 4, respectively.

Among the images provided for the latter purpose, the lower horizontal flange 16 has a nearly semicircular outline (FIGS. 6 and 7), which is substantially repeated by the overlying oblique flange 17 (FIGS. 4 and 7),. Between the flanges 16 and 17, and the vertical distal flanges 18 and 19 (FIG. 7) a nearly semi-annular space 22 is defined, the height of which can be varied linearly (FIGS. 4 and 7), which communicates with the inner chamber 12 of the cylindrical head 8 through a similarly shaped opening 23 (FIGS. 1 and 4) and confronts the inlet slot or port 3 so as to communicate therewith in a linearly variable manner, the variation being a function of the angular position of the rotatable body 7, and is more exactly at a minimum when the right end (as viewed in FIGS. 4 and 7) of the variable-height chamber 22 is in confronting relationship with the slot 3 and is at a maximum when the other end is in the position as indicated just now.

In a position which is substantially symmetrical with respect to the flange 17, but with an opposite slope (FIG. 5), the other sloping flange 20 is arranged, which, in combination with the flange 16 defines at the top the space which surrounds the tube 11 and the cylindrical body 10 and causes the latter to communicate with the outlet slot or port 4 to a degree which varies linearly as a function of the angular position of the rotatable body 7. More exactly, such a degree is at a minimum when the lowest end of the flange 20 is in confronting relationship with the slot 4, and is, conversely, at a maximum when the uppermost end of the flange confronts the slot 4 (on account of the concordant variation of height, FIG. 7, a variation of the angular position of the rotatable body causes concordant variations of the width of the communication between the inlet port 3 and the variable-height space 22 and between the space 24 underlying the flanges 20 and 16 and the outlet port 4).

Above all of the other flanges 16-20, lastly, there is arranged the horizontal annular flange 21 (FIGS. 2, 4 and 5), which, in combination with the two sloping flanges 16 and 20 defines an annular communication passageway directly between the inlet and the outlet ports 3 and 4, respectively. Such a passageway provides, more particularly, an inlet space 25 (FIG. 3) and an outlet space 26 (FIG. 5), the height of which varies as the angular position of the rotatable body 7 is varied. The variation is concordant for the spaces 25 and 26 with respect to one another, but is discordant relative to the height variations of the spaces 22 and 24 (FIGS. 4 and 5). The portions of the spaces 25 and 26 which are confronting and thus in communication with the inlet and outlet ports 3 and 4, have thus a variable size, the latter variation taking place in a way which is discordant with that of the corresponding portions of the spaces 22 and 24 as a function of the angular position of the rotatable body 7.

Figure 3:
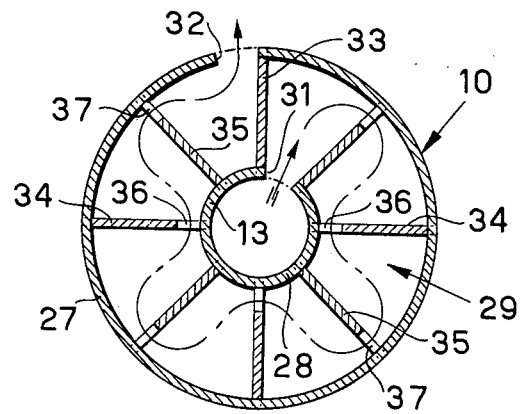
FIG. 3 shows the detail viewes, in cross-sectional horizontal view, taken along the line III—III of FIG. 1, of the cylindrical body defining the portion of labyrinthic route in which the breathable product sweeps the anaestethic product.

Lastly, the cylindrical body 10 comprises two coaxial cylindrical walls 27 and 28, which define therebetween an annular space 29: the latter is open at the bottom and is closed at the top by a horizontal annular wall 30 (FIGS. 1 and 3). Such an annular space communicates through openings 31 and 32 with the inner cylindrical space 13 and with the outer annular space 24 in correspondence with two ends as defined at the two sides of a radial partition wall 33 and is made sinuous (FIG. 3) by a series of radial paddles 34 and 35, which have alternatingly arranged openings 36 and 37 in correspondence with their inner and outer ends.

The foregoing description clearly shows that the configuration, as described hereinabove, of the rotatable body 7 and more particularly of the flanged head 8 and the cylindrical body 10, acts in such a way that for the flow of the breathable product which enters through the inlet slot or post 3, there are defined two discrete passageways for communication with the outlet slot or port 4. Either of these passagways is constituted by the annular passageway as confined between the flanges 21, 17, 20 of the cylindrical head 8 and thus affords a direct communication between the mouths 3 and 4. The other passageway, conversely, is formed by the variable-height space 22, the opening 23, the inner chamber 12 of the cylindrical head 8, the inner passageway of the vertical tube 11, the inner space 13 of the cylindrical body 10, the sinuous annular space 29 of the same cylindrical body, and, finally, by the annular space 24 as confined at its top by the flanges 16 and 20. Such passages are simultaneously and complementarily throttled by a variation of the angular position of the rotatable body 7.

The rectilinear outline, which unfolds through almost 180°, of the slanting flanges 17 and 20 guarantee a very fine adjustment of the non-concordantly variable degree of communication between the ports 3 and 4, the direct passageway 25, 26, and also the communication width between the ports 3 and 4 and the deflected path 22, 12, 19, 24.

As a result, while a variable portion of the stream of incoming breathable product is transferred directly of the outlet without being admixed with the anaesthetic product, the residual portion of the same stream of breathable produce is deflected towards the sinuous annular space 29, wherein it sweeps the anaesthetic product 2 so as to cause the evaporation of same and strip the vapors which are thusly evolved. The portion of the breathable product which emerges from the outlet slot 4 coming from the space 24 is thus supplemented by the anaesthetic product. As the two direct and deflected streams merge at the outlet of the evaporator, the overall steam issuing from the evaporator is thus composed by an admixture of breathable product and anaesthetic product, the admixing proportions of which are obviously a function of the degree of complementary throttling of the two routes, the direct one and the deflected one, and thus of the angular position of the rotatable body 7. The rectilinear outline and the almost semicircular outline of the slanting flanges 17 and 20 make such a degree of admixture both linearly and finely variable, whereas the labyrinth-like shape of the deflected path portion formed by the sinuous space 29 makes comparatively wider the contact surface between the breathable product and the anaesthetic product, and thus improves the capacity of evaporation and stripping of the anaesthetic product, the setting of the rotatable body 7 being the same.

What is claimed is:

1. A mixing evaporator for anaesthetic products, comprising a vessel for containing in the lower portion thereof a liquid vaporizable anaesthetic product, said vessel having an inlet port formed through the upper portion thereof to permit the intake of a stream of a breathable gas and an outlet port formed through the upper portion thereof to permit the outflow of the same stream of a breathable product supplemented by an anaesthetic product in a variable proportion; means in said vessel defining two discrete passageways either of which directly connects the inlet port and outlet ports so as to convey breathable gas from the inlet port to the outlet port without addition of vaporizable product to the gas and the other of which connects these same ports and includes a deflected portion in communication with the lower portion of the vessel so as to contact and evaporate a portion of the vaporizable product in the lower portion of the vessel, said means including a rotatable body housed in said vessel, said rotatable body forming said passageways and cooperating with the wall of said vessel to throttle said passageways, said body including a depending vertical tubular portion extending into the lower portion of said vessel and terminating in a cylindrical body which is immersible in vaporizable anaesthetic product; said cylindrical body including an inner tubular wall forming a chamber in communication with said depending tubular portion and an outer concertric tubular wall, said tubular walls defining an annular space which is closed at the top and open at the bottom, an imperforate radial partition connected between said concentric walls thereby forming said annular space into a passage, said inner concentric wall having an opening at one side of said partition and said outer concentric wall having an opening therein on the other side of said partition, and a plurality of radial paddles in said annular space having alternately arranged openings therein so that a flow path through said passage is tortuous, said passage forming part of said deflected portion of said other passageway.

2. A mixing evaporator as in claim 1 wherein said rotatable body has an inner chamber in comunication with the upper end of said vertical tubular portion; said rotatable body having of lower horizontal flange of nearly semicircular width, an overlying sloping flange of like width, and vertical flanges at the ends of said horizontal flange and said semicircular flange and cooperating therewith to define a nearly half-annular space which has a linearly variable height communicating through an opening in said rotatable body with said inner chamber, said half-annular space being in confronting relationship with the inlet port of said vessel so as to communicate therewith in a linearly variable manner as a function of the position of said rotatable body; said rotatable body having a further sloping flange having a nearly semicircular width arranged symmetrically relative to said first-mentioned sloping flange and with an opposite slope, said further sloping flange cooperating with said lower horizontal flange to form a space which surrounds said vertical tubular portion of said rotatable head, which communicates with the opening in said outer concentric wall of said cylindrical body and which is in confronting relationship with the outlet port of said vessle so as to communicate therewith in a linearly variable manner as a function of the position of said rotatable body; and said rotatable body having a top annular flange which cooperates with said sloped flanges to define said direct connection between the inlet port and the outlet port of said vessel.

* * * * *